(12) United States Patent
Matsumoto et al.

(10) Patent No.: US 10,605,715 B2
(45) Date of Patent: Mar. 31, 2020

(54) FLOW CYTOMETER AND PARTICLE DETECTION METHOD

(71) Applicant: SYSMEX CORPORATION, Kobe-shi, Hyogo (JP)

(72) Inventors: Shohei Matsumoto, Kobe (JP); Tomoya Hayashi, Kobe (JP)

(73) Assignee: SYSMEX CORPORATION (JP)

( * ) Notice: Subject to any disclaimer, the term of this patent is extended or adjusted under 35 U.S.C. 154(b) by 0 days.

(21) Appl. No.: 16/365,964

(22) Filed: Mar. 27, 2019

(65) Prior Publication Data

US 2019/0301993 A1 Oct. 3, 2019

(30) Foreign Application Priority Data

Mar. 30, 2018 (JP) .................................. 2018-067088

(51) Int. Cl.
*G01N 15/14* (2006.01)
*G01N 15/10* (2006.01)
*G01N 35/00* (2006.01)
*B01F 3/08* (2006.01)

(52) U.S. Cl.
CPC ..... *G01N 15/1404* (2013.01); *G01N 15/1012* (2013.01); *G01N 15/1425* (2013.01); *G01N 15/1459* (2013.01); *B01F 3/0865* (2013.01); *G01N 2015/1006* (2013.01); *G01N 2015/1018* (2013.01); *G01N 2035/00544* (2013.01)

(58) Field of Classification Search
CPC ....... G01N 15/1404; G01N 2015/1409; G01N 2015/1411; G01N 2015/1006
See application file for complete search history.

(56) References Cited

U.S. PATENT DOCUMENTS

| 5,895,764 A | * | 4/1999 | Sklar | ................. | G01N 15/1404 |
| | | | | | 356/317 |
| 6,473,171 B1 | * | 10/2002 | Buttry | .................... | G01N 15/14 |
| | | | | | 356/246 |
| 6,507,391 B2 | * | 1/2003 | Riley | ................. | G01N 15/1012 |
| | | | | | 356/28 |
| 2003/0142289 A1 | | 7/2003 | Ortyn et al. | | |
| 2005/0105077 A1 | * | 5/2005 | Padmanabhan | .... | G01N 15/1484 |
| | | | | | 356/39 |
| 2012/0070818 A1 | * | 3/2012 | Rowlen | .............. | G01N 15/1404 |
| | | | | | 435/3 |
| 2018/0024039 A1 | * | 1/2018 | Azuma | .................. | G01N 15/14 |
| | | | | | 435/29 |
| 2018/0156710 A1 | * | 6/2018 | Vrane | ................ | G01N 15/1434 |

FOREIGN PATENT DOCUMENTS

| EP | 2347243 A1 | 7/2011 |
| WO | WO2002/017219 | 2/2002 |
| WO | 2010/043917 A1 | 4/2010 |

OTHER PUBLICATIONS

The extended European search report dated Sep. 18, 2019 in a counterpart European patent application No. 19163683.6.

* cited by examiner

*Primary Examiner* — Maurice C Smith
(74) *Attorney, Agent, or Firm* — Brinks Gilson & Lione

(57) ABSTRACT

The present invention is to provide a flow cytometer comprising: flow cell; a liquid feeding unit for feeding a liquid different from a sample liquid containing sample particles to the flow cell; a sample liquid feeding unit for feeding the sample liquid to the flow cell after the liquid is sent to the flow cell; and a detector for detecting the sample particles flowing through the flow cell.

22 Claims, 11 Drawing Sheets

FLOW CYTOMETER AND PARTICLE DETECTION METHOD

RELATED APPLICATIONS

This application claims priority from prior Japanese Patent Application No. 2018-067088, filed on Mar. 30, 2018, entitled "Flow Cytometer and Particle Detection Method", the entire contents of which are incorporated herein by reference.

BACKGROUND OF THE INVENTION

1. Field of the Invention

The present invention relates to a measurement technique, and relates to a flow cytometer and a particle detection method.

2. Description of the Related Art

Flow cytometers are widely used for analysis of biological samples such as cells and microorganisms. In a flow cytometer, a biological sample flowing inside a transparent flow cell is optically analyzed. In the interior of the flow cell, the flow of a sample liquid containing the biological sample and the flow of a sheath liquid form a laminar flow so that the flow of the sample liquid is in the flow of the sheath liquid which is in contact with the inner wall of the flow cell. By adjusting the pore size of the flow cell and the supply amount of the sample liquid and the sheath liquid, it is possible to flow biological samples one by one into the flow cell. According to the flow cytometer, it is therefore possible to optically analyze each one of the biological samples constituting the biological sample population.

In order to optically and accurately analyze a biological sample flowing inside the flow cell, it is desirable to appropriately set the flow velocity of the biological sample flowing inside the flow cell according to the capability of the optical analysis apparatus. For example, in U.S. Pat. No. 6,507,391, light is irradiated on particles inside a flow cell, scattered light and fluorescent light generated in the particles are modulated by an optical grating, and the flow velocity of particles flowing inside the flow cell is calculated based on a detection cycle of modulated light. U.S. Pat. No. 6,507,391 also discloses a TDI (Time Delay Integration) imaging method for imaging particles by synchronizing the charge transfer timing in a charge coupled device (CCD) array to the calculated particle velocity.

SUMMARY OF THE INVENTION

When analyzing a biological sample with a flow cytometer, it is desirable to start optical analysis of sample particles in a state in which the flow velocity of the sample particles flowing inside the flow cell is stable.

However, the sample particles that flow prior to the flow velocity becoming stable are wasted without being analyzed. Some sample particles, for example, blood circulating tumor cells (CTC) are contained in the sample solution only a little, and there is demand for a technology that can perform analysis without wasting sample particles contained in the sample solution. Therefore, the present invention provides a flow cytometer and a particle detection method capable of suppressing waste of sample particles.

According to an aspect of the present invention, a flow cytometer including a flow cell 10, a liquid feeding unit 30 for feeding a liquid different from the sample liquid containing the sample particles to the flow cell 10, a sample feeding unit 20 for feeding the sample liquid to the flow cell 10 after the liquid is sent to the flow cell 10, and a detector 201 for detecting sample particles flowing through the flow cell 10 is provided.

According to the above flow cytometer, it becomes possible to stabilize the liquid feeding drive to the flow cell 10 while feeding a liquid different from the sample liquid to the flow cell 10, and thereafter the sample liquid is fed to the flow cell 10. Therefore, it is possible to prevent the sample liquid from being wasted due to flowing of the sample liquid until the flow velocity in the flow cell 10 becomes stable.

In the above-described flow cytometer, the liquid feeding unit 30 and the sample liquid feeding unit 20 may respectively feed a liquid different from the sample liquid and the sample liquid to the flow cell 10 via a common flow path. The liquid feeding unit 30 may be a reference liquid feeding unit that delivers a reference liquid containing reference particles different from the sample particles as a liquid different from the sample liquid to the flow cell. Even after the sample liquid feeding unit 20 starts feeding the sample liquid to the flow cell 10, the reference liquid feeding unit may feed the reference liquid to the flow cell 10. After the sample liquid feeding unit 20 starts feeding the sample liquid to the flow cell 10, the sample liquid feeding unit 20 may increase the volume of the sample liquid to be fed, and the reference liquid feeding unit may decrease the volume of the reference liquid to be fed so that the total flow velocity of the combined flow velocity of the sample liquid and the flow velocity of the reference liquid fed to the flow cell 10 becomes constant.

The above flow cytometer may also include a flow velocity measuring device 200 for acquiring information on the flow velocity of the liquid flowing through the flow cell 10, and the sample liquid feeding unit 20 may feed the sample liquid to the flow cell 10 when the information on the flow velocity meets a criterion.

According to the above flow cytometer, when the information on the flow velocity satisfies the criterion, the sample liquid is sent to the flow cell 10, so that the sample liquid is not wasted before the information on the flow velocity satisfies the criterion.

The flow cytometer also may feed a liquid different from the sample liquid to the flow cell 10 by the liquid feeding unit until the information on the flow velocity satisfies the criterion.

According to the above flow cytometer, a liquid different from the sample liquid is fed to the flow cell 10 until the information on the flow velocity satisfies a criterion, so that the sample liquid is not wasted before the information on the flow velocity satisfies the criterion.

In the above flow cytometer, the information on the flow velocity may be at least one of the value of the flow velocity and the value of the fluctuation of the flow velocity. When the information on the flow velocity is the value of the flow velocity and the value of the flow velocity is within a predetermined range, the sample liquid feeding unit 20 also may feed the sample liquid to the flow cell 10. When the information on the flow velocity is the value of the fluctuation of the flow velocity and the value of the fluctuation of the flow velocity is a predetermined value or less, the sample liquid feeding unit 20 also may feed the sample liquid to the flow cell 10. The fluctuation of the flow velocity may be a coefficient of variation of the flow velocity.

According to the above flow cytometer, when the value of the flow velocity is within a predetermined range or the value of variation in the flow velocity is a predetermined value or less, the sample liquid is fed to the flow cell 10, so that the flow velocity of the sample liquid is stabilized when the sample particles are measured.

The flow cytometer also includes a control unit 302 that causes the sample liquid to be fed to the flow cell 10 by the sample liquid feeding unit 20 when the information on the flow velocity satisfies the criterion, and does not cause the sample liquid to be fed to the flow cell 10 by the sample feeding unit 20 when the information on the flow velocity does not satisfy the criterion.

According to the above flow cytometer, it is possible to control the sample liquid feeding unit 20 so that the sample liquid is not wasted.

The flow cytometer also may include an output device 401 for outputting information indicating that the information on the flow velocity does not satisfy the criterion when the information on the flow velocity does not satisfy the criterion. When the information on the flow velocity does not satisfy the criterion, the output device 401 also may output information for inquiring whether to stop feeding the sample liquid to the flow cell 10.

According to the above flow cytometer, the operator can comprehend the state of the flow cytometer and determine whether the analysis by the flow cytometer can proceed.

In the above-described flow cytometer, the liquid feeding unit 30 feeds a liquid different from the sample liquid at a first flow velocity to the flow cell 10, and then, feeds the liquid different from the sample liquid at a second flow velocity that is less than the first flow velocity to the flow cell 10.

For example, in a sheath flow type flow cytometer, when particles are supplied to a flow cell after starting the flow of a sheath liquid to the flow cell, there is concern that the particles supplied to the flow cell may flow backward since the flow cell side is in a state of high pressure due to the supply of the sheath liquid. In order to prevent such reverse flow, it is preferable to carry out a process called pre-drive in which the liquid is initially supplied at a high flow after the sheath liquid is supplied to the flow cell. Here, when a high flow velocity of sample liquid is flowed in the pre-drive, valuable sample liquid is wasted. On the other hand, according to the above flow cytometer, pre-drive is performed at the first flow velocity using a liquid different from the sample liquid, so that waste of the sample liquid can be suppressed.

The above flow cytometer also includes a sample liquid flow path 51 which is connected to the sample liquid feeding unit 20 and through which the sample liquid flows, a liquid flow path 52 which connects the sample flow path 51 and the liquid feeding unit 30 and through which a liquid that is different from the sample liquid flows, a supply flow path 53 which connects the sample liquid flow path 51 and the flow cell 10 and through which flows the sample liquid and the liquid that is different from the sample liquid, wherein the sample liquid may be supplied into the sample liquid flow path 51 from an open end 55 of the sample liquid flow path 51. After the sample liquid feeding unit 20 suctions the sample liquid from a connection point 56 of the sample liquid flow path 51 and the liquid flow path 52 to the sample liquid feeding unit 20 side, the liquid feeding unit 30 may feed the liquid different from the sample liquid to the flow cell 10.

According to the flow cytometer described above, it is possible to feed a liquid different from the sample liquid to the flow cell 10 while holding the sample liquid therein.

In the above-described flow cytometer, the sample liquid feeding unit 20 also may suction air while the internal liquid fills inside of the sample liquid flow path 51, and the sample liquid may be suctioned following the air.

For example, in a sheath flow type flow cytometer, when the sheath liquid is started to flow at high pressure to the flow cell, the pressure of the air existing between the internal liquid and the sample liquid in the sample liquid flow path fluctuates. Therefore, if feeding of the sample liquid is started without sending a liquid that is different from the sample liquid after sending the sheath liquid, the flow speed of the sample liquid becomes unstable due to the pressure fluctuation of the air inside the sample liquid flow path, and it is difficult to accurately detect the sample particles contained in the sample liquid. Conversely, according to the above-described flow cytometer, since a liquid different from the sample liquid is fed before feeding the sample liquid, the pressure fluctuation of the air inside the sample liquid flow path 51 is reduced during feeding of a liquid different from the sample liquid. Therefore, when the feeding of the sample liquid is started, the flow velocity of the sample liquid is not readily influenced by the air pressure fluctuation.

In the above flow cytometer, the flow velocity measuring device 200 may measure the flow velocity based on the optical characteristics of the particles flowing through the flow cell 10. In the flow cytometer, the flow velocity measuring device 200 includes a light source 121 that irradiates light on the flow cell 10, and a reactive light detecting unit 161 that detects reactive light generated by particles irradiated with light inside the flow cell 10. The flow velocity measuring device 200 also may include an optical grating 151 disposed between the flow cell 10 and the reactive light detecting unit 161 to modulate the reactive light. The reactive light may be scattered light.

According to the above flow cytometer, it is possible to accurately measure the flow velocity of particles flowing inside the flow cell 10.

In the above flow cytometer, the sample particle may be a biological sample and the reference particle may be a non-biological particle. The sample particles may be blood circulating tumor cells.

According to the above flow cytometer, it is possible to stabilize the flow velocity inside the flow cell 10 by using non-biological particles, so as to suppress waste of biological samples. It also is possible to suppress the waste of rare blood circulating tumor cells.

In the above-described flow cytometer, the detector 201 may be a particle imaging unit for imaging sample particles.

According to the above flow cytometer, it is possible to image particles flowing at a stable velocity through the flow cell 10.

According to an aspect of the present invention, a particle detection method is provided which includes feeding a liquid that is different from the sample liquid containing the sample particles to the flow cell 10, feeding a sample liquid to the flow cell 10 after the liquid that is different from the sample liquid is fed to the flow cell 10, and detecting the sample particles flowing through the flow cell 10.

According to the above particle detection method, it becomes possible to stabilize the liquid feeding drive to the flow cell 10 while feeding a liquid different from the sample liquid to the flow cell 10, and thereafter the sample liquid is fed to the flow cell 10. Therefore, it is possible to prevent the sample liquid from being wasted due to flowing of the sample liquid until the flow velocity in the flow cell 10 becomes stable.

In the above particle detection method, the liquid different from the sample liquid is a reference liquid containing reference particles, and the method also includes acquiring information on the flow velocity of the reference liquid flowing through the flow cell 10, and feeding the sample liquid to the flow cell 10 when the information on the flow velocity satisfies a criterion.

According to the above particle detection method, the sample liquid is fed to the flow cell 10 when the information on the flow velocity satisfies the criterion, so that the sample liquid is not wasted before the information on the flow velocity satisfies the criterion.

DETAILED DESCRIPTION OF THE PREFERRED EMBODIMENTS

Figure 1:
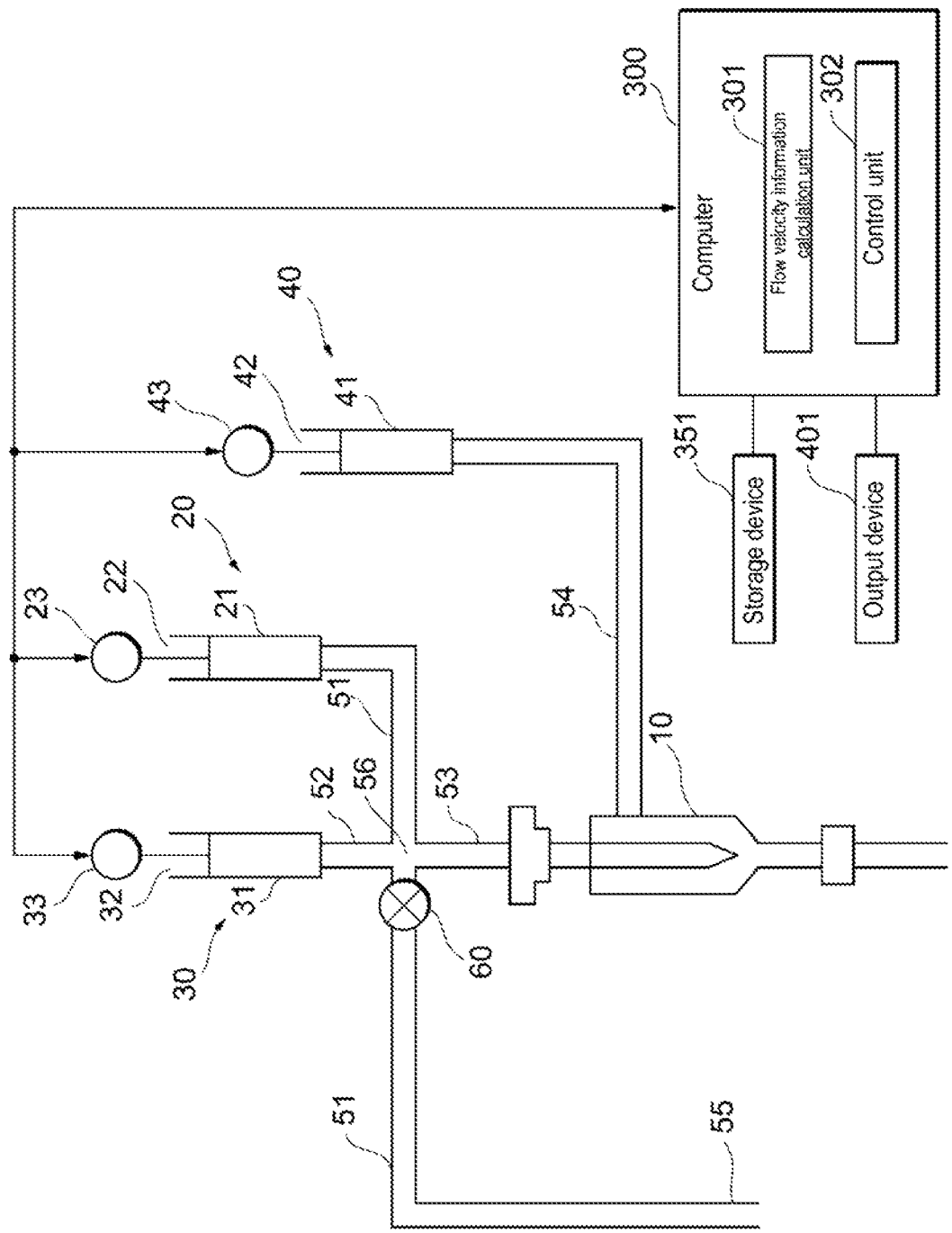
FIG. 1 is a schematic diagram showing a flow path and the like of a flow cytometer according to an embodiment.

Hereinafter, embodiments of the present invention will be described with reference to the drawings. In the following description of the drawings, the same or similar parts are denoted by the same or similar reference numerals. However, the drawings are schematic. Therefore, concrete dimensions and the like should be determined in light of the following explanation. It is a matter of course that the drawings also include parts having different dimensional relationships and ratios.

In the embodiment described below, the present invention is applied to an apparatus for imaging blood circulating tumor cells (CTC: Circulating Tumor Cell) contained in a blood specimen. Advanced cancer cells circulate on the flow of blood and lymph, and metastasize to distant organs. CTC circulating in the blood is extremely small, and only several to several tens of CTC exist in 10 mL of blood. Detection of CTC in the blood is recognized as useful for determination of therapeutic effect and prediction of prognosis in metastatic cancer patients such as breast cancer, prostate cancer and colon cancer.

Figure 2:
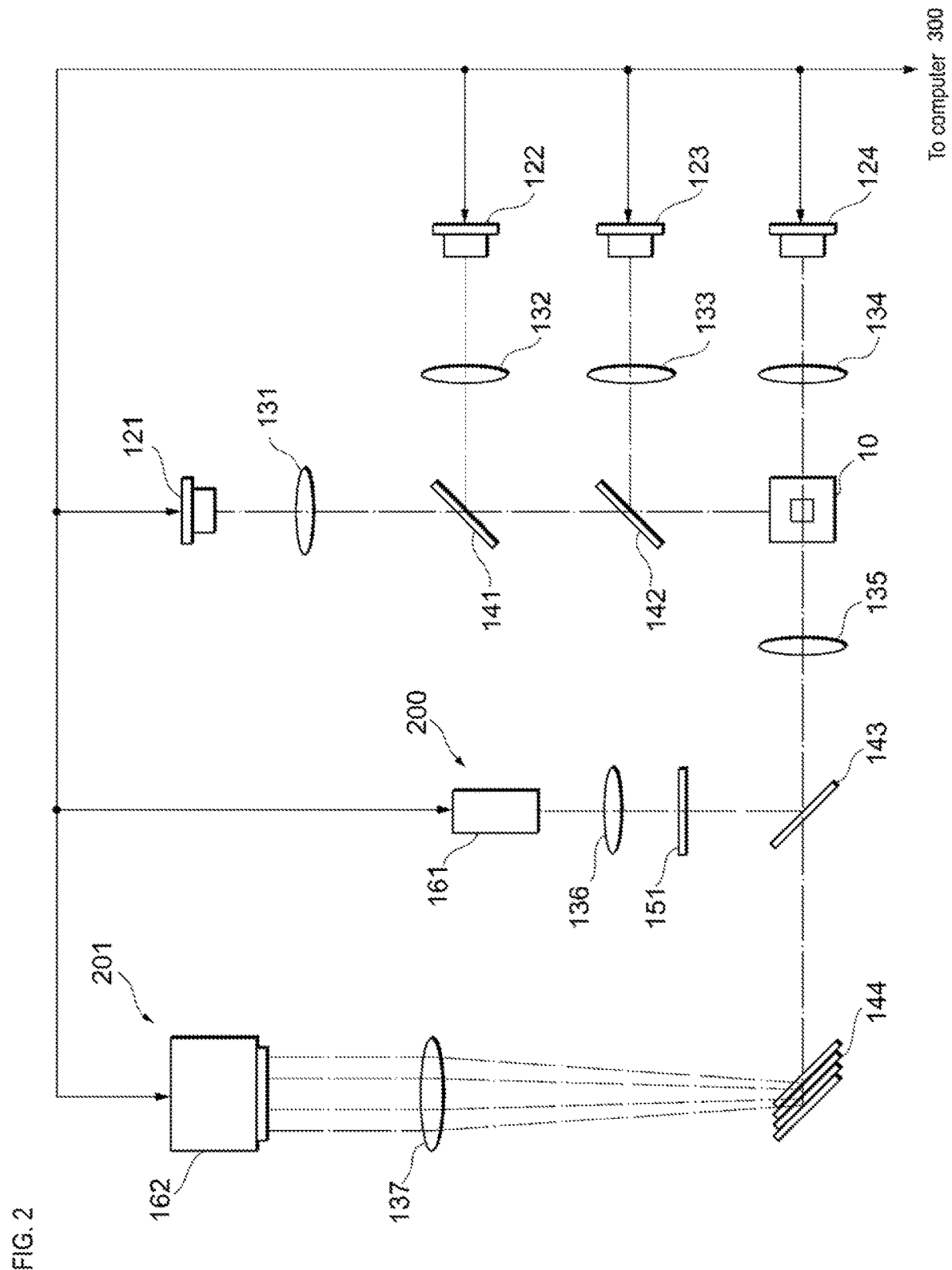
FIG. 2 is a schematic diagram showing an optical system and the like of a flow cytometer according to an embodiment.

As shown in FIG. 1, the flow cytometer according to the embodiment includes a flow cell 10, a liquid feeding unit 30 for feeding a liquid different from the sample liquid containing sample particles to the flow cell 10, a sample feeding unit 20 for feeding the sample liquid to the flow cell 10 after the liquid is sent to the flow cell 10, and a detector 201, shown in FIG. 2, for detecting sample particles flowing through the flow cell 10.

The sample particles are particles whose characteristics are analyzed with a flow cytometer, and in this embodiment they are CTC. The sample liquid containing CTC is a blood sample. The blood sample is treated with, for example, a virus that is integrated with a green fluorescent protein (GFP) gene and that specifically proliferates within cancer cells. If CTC is included in the blood sample, CTC infects the virus and fluorescent protein is expressed in CTC. The CTC may be labeled with an antigen-specific fluorescent probe. Alternatively, the CTC may be stained with a reagent containing a Ch17 probe that binds to chromosome 17, and a Her2 probe that binds to the Her2 gene.

The liquid different from the sample liquid is, for example, a reference liquid containing reference particles different from the sample particles. The reference particles are non-biological particles for monitoring the flow velocity of the particles flowing inside the flow cell 10, and are composed of, for example, a polymer such as latex, an inorganic substance, or the like. The reference particle has, for example, an optical characteristic that generates scattered light stronger than the sample particle when it is irradiated with light. The reference liquid containing reference particles is, for example, a buffer solution.

The flow cytometer according to the embodiment also may include a flow velocity measuring device 200 shown in FIG. 2 for acquiring information on at least the flow velocity of the reference liquid flowing inside the flow cell 10. In the flow cytometer according to the embodiment, the liquid feeding unit 30 shown in FIG. 1 feeds the reference liquid to the flow cell 10 until the information on the flow velocity satisfies a criterion. When the information on the flow velocity satisfies the criterion, the sample liquid feeding unit 20 starts to feed the sample liquid to the flow cell 10. Note that the liquid feeding unit 30 also may feed the reference liquid to the flow cell 10 even after the information on the flow velocity satisfies the criterion. A time period during which the flow velocity can be stabilized may be acquired in advance, and after that time, the sample liquid feeding unit 20 may start to feed the sample liquid to the flow cell 10. In this case, it is not necessary to measure the flow velocity. The flow cytometer according to the embodiment also includes a sheath liquid feeding unit 40 for feeding a sheath liquid to the flow cell 10.

The flow cytometer according to the embodiment also includes a sample liquid flow path 51 which connects to the sample liquid feeding unit 20 and through which the sample liquid flows, a liquid flow path 52 which connects the sample liquid flow path 51 and the liquid feeding unit 30 and through which the reference liquid flows, and a supply flow path 53 which connects the sample liquid flow path 51 and the flow cell 10 and through which the sample liquid and the liquid that is different from the sample liquid flows. The liquid flow path 52 and the supply flow path 53 are connected to the sample liquid flow path 51 at the same connection point 56. Alternatively, the liquid flow path 52 and the supply flow path 53 also may be connected to the sample liquid flow path 51 at different connection points. The flow cytometer according to the embodiment also includes a sheath liquid flow path 54 which connects the sheath liquid feeding unit 40 and the flow cell 10, and through which a sheath liquid flows.

The sample liquid feeding unit 20 includes, for example, a syringe 21, an actuator 22 such as a plunger and a piston inserted in the syringe 21, and a drive device 23 such as a motor for moving the actuator 22. Note that the sample liquid feeding unit 20 may be a diaphragm pump or a sample liquid may be fed using an air pressure generated by an electropneumatic converter connected to a pressure source such as a compressor.

Figure 3:
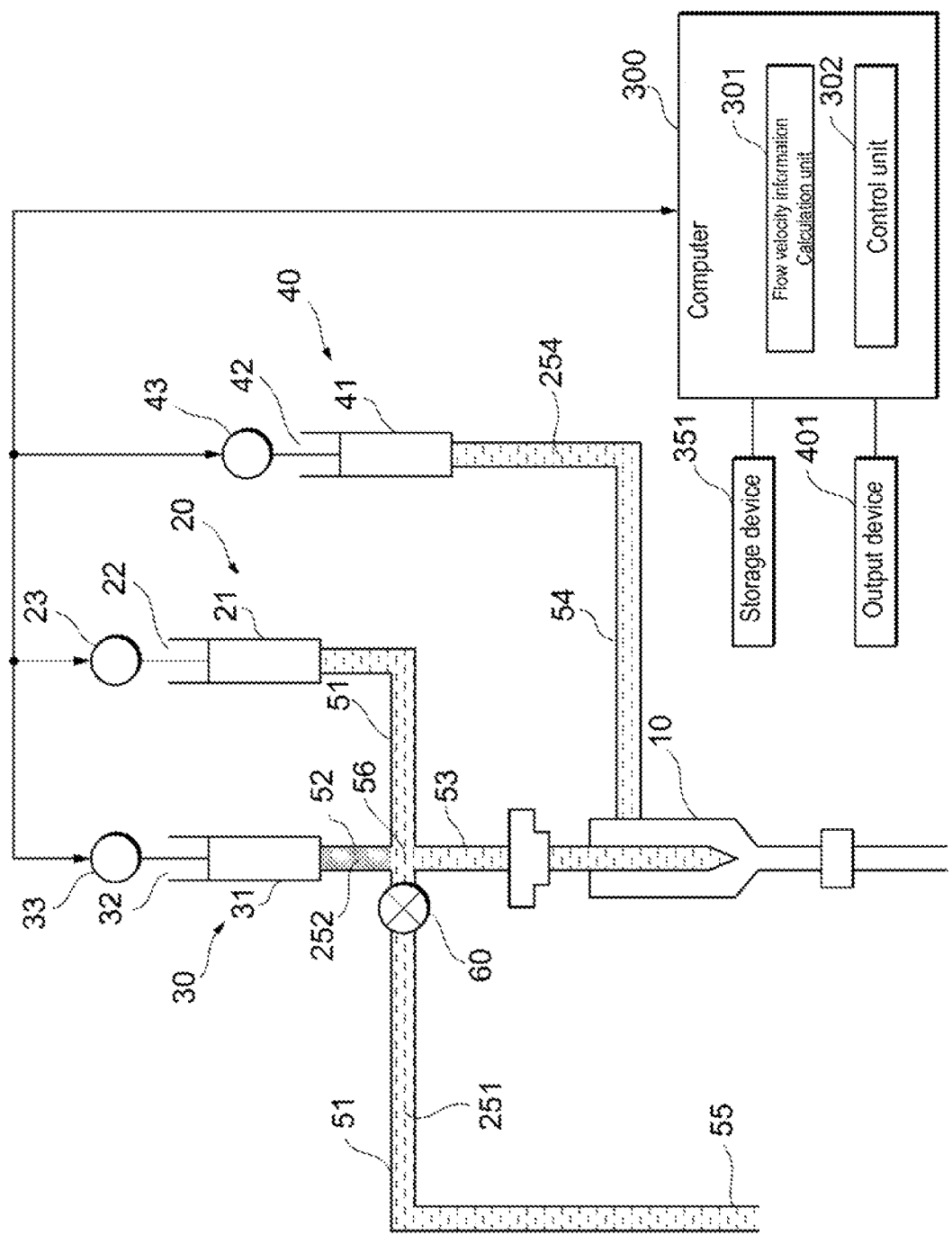
FIG. 3 is a schematic view showing a flow path and the like of a flow cytometer according to an embodiment.
Figure 4:
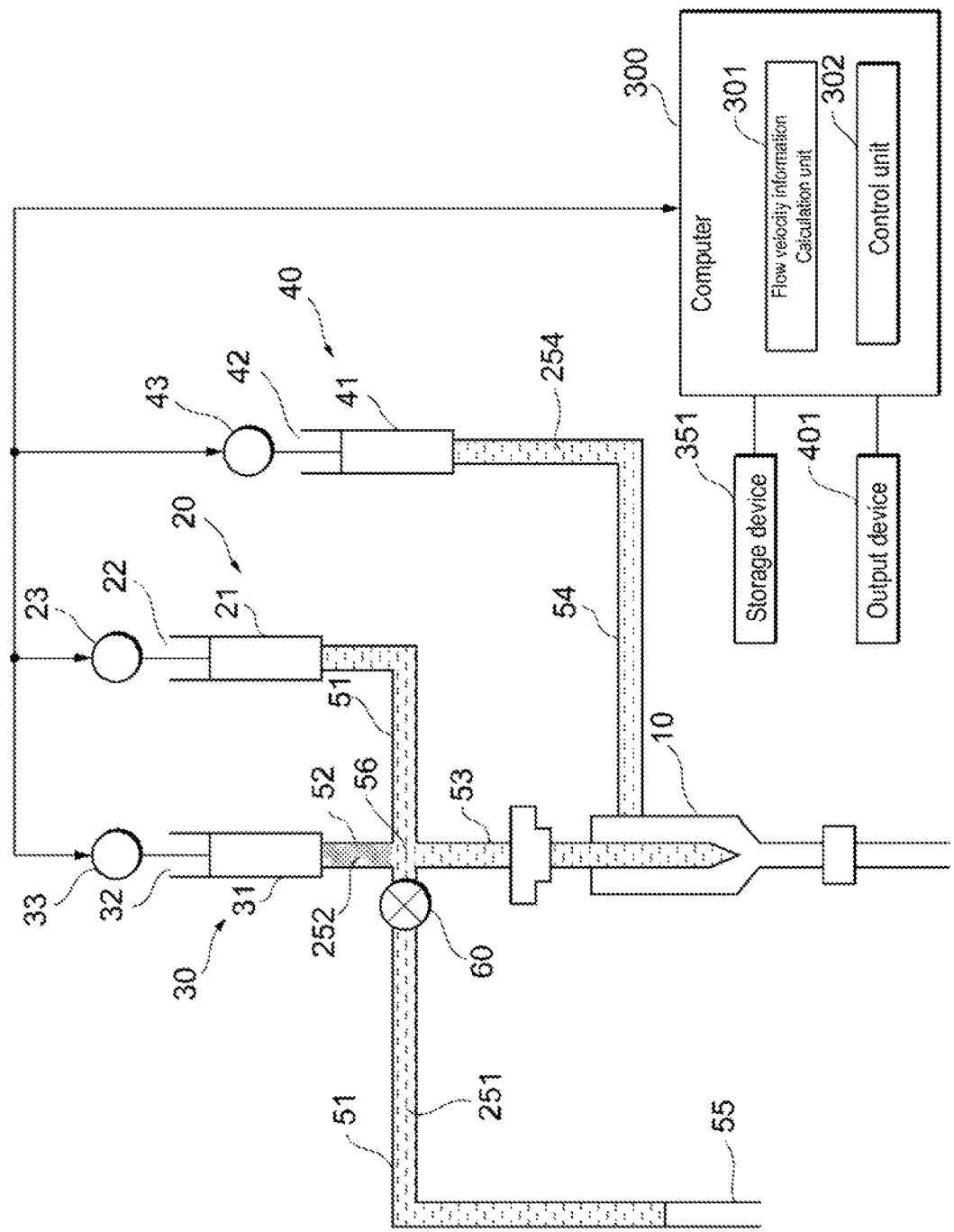
FIG. 4 is a schematic diagram showing a flow path and the like of a flow cytometer according to an embodiment.
Figure 5:
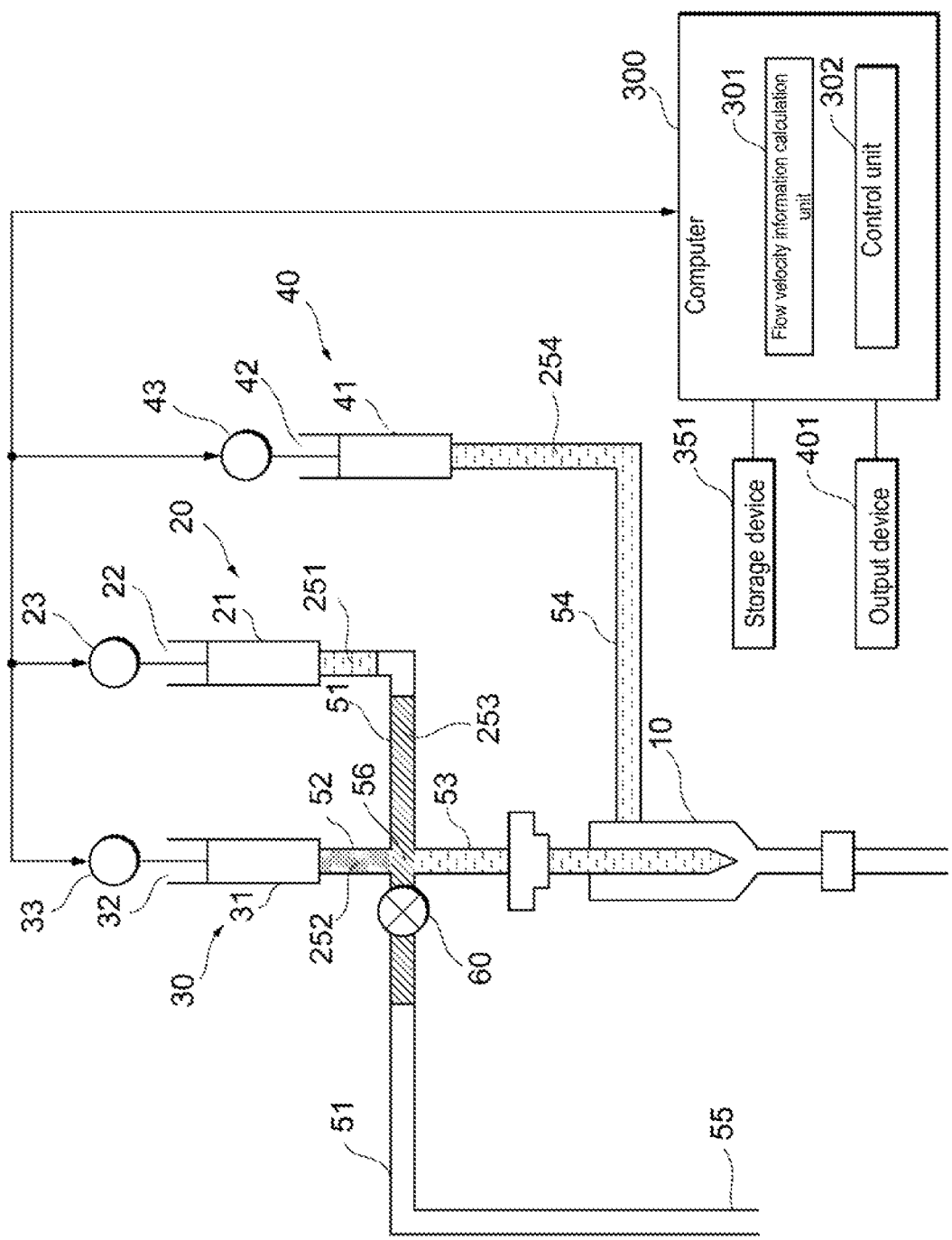
FIG. 5 is a schematic diagram showing flow paths and the like of the flow cytometer according to the embodiment.

As shown in FIG. 3, prior to the start of detection of the sample particles, the sample liquid flow path 51 and the supply flow path 53 are filled with an internal liquid 251 such as a buffer solution, and in the sheath liquid flow path 54 is filled with a sheath liquid 254. The sheath liquid 254 is, for example, a buffer solution and has the same composition as the internal liquid 251. The liquid flow path 52 is filled with a reference liquid 252. When the drive device 23 of the sample liquid feeding unit 20 pulls the actuator 22, air is suctioned from the open end 55 of the sample liquid flow path 51 as shown in FIG. 4. Thereafter, the open end 55 of the sample liquid flow path 51 is inserted into the sample container in which the sample liquid 253 is stored, and as shown in FIG. 5, the sample liquid feeding unit 20 suctions the sample liquid 253 from the sample container so as to produce an air layer between the sample liquid 253 and the internal liquid 251 in order not to dilute the concentration of the sample liquid 253 by mixing the sample liquid 253 and the internal liquid 251.

For example, within the sample liquid flow path 51, the sample liquid feeding unit 20 suctions the sample liquid to the sample liquid feeding unit 20 side from the connection point 56 of the sample liquid flow path 51, the liquid flow path 52, and the supply flow path 53. Note that a part of the sample liquid may remain on the open end 55 side of the connection point 56 in order to prevent air from entering the supply flow path 53. When the liquid flow path 52 and the supply flow path 53 are connected to the sample liquid flow path 51 at different connection points, the sample liquid feed unit 20 suctions the sample liquid toward the sample liquid feeding unit 20 side from the connection point on the side close to the sample liquid feeding unit 20 side within the sample liquid flow path 51. Note that a part of the sample liquid may remain on the open end 55 side of the connection point.

A valve 60 is provided in the sample liquid flow path 51. When the liquid flow path 52 and the supply flow path 53 are connected to the sample liquid flow path 51 at the same connection point 56, the valve 60 is located in the vicinity of the connection point 56 on the open end 55 side of the sample liquid flow path 51 from the connection point 56. When the liquid flow path 52 and the supply flow path 53 are connected to the sample liquid flow path 51 at different connection points, the valve 60 is located near the connection point on the open end 55 side, from the connection point. The valve 60 is opened when suctioning the sample liquid into the sample liquid flow path 51 from the open end 55. The valve 60 is closed after, in the sample liquid flow path 51, the sample liquid is suctioned toward the sample liquid feeding unit 20 side from the connecting point 56 or the connecting point closer to the sample liquid feeding unit 20.

Figure 6:
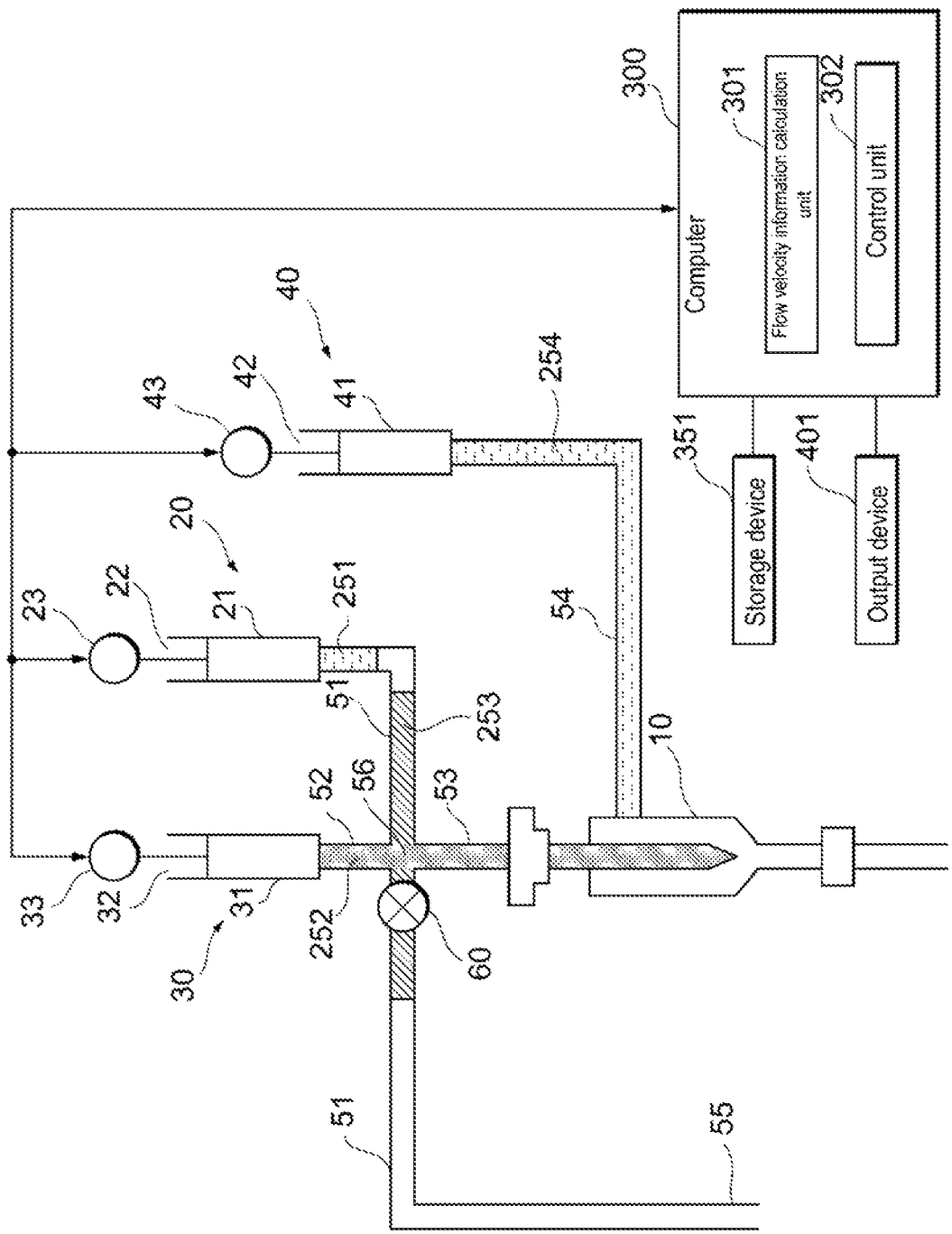
FIG. 6 is a schematic diagram showing flow paths and the like of the flow cytometer according to the embodiment.

After the valve 60 is closed, the sheath liquid feeding unit 40 feeds the sheath liquid to the flow cell 10 and, as shown in FIG. 6, the liquid feeding unit 30 feeds the reference liquid to the flow cell 10. After the sheath liquid feeding unit 40 starts feeding the sheath liquid to the flow cell 10, the liquid feeding unit 30 starts feeding the reference liquid to the flow cell 10. At the same time that the sheath liquid feeding unit 40 starts feeding the sheath liquid to the flow cell 10, the liquid feeding unit 30 also may start feeding the reference liquid to the flow cell 10.

The liquid feeding unit 30 includes, for example, a syringe 31, an actuator 32 inserted into the syringe 31, and a drive device 33 such as a motor for moving the actuator 32. When the drive device 33 presses the actuator 32, the reference liquid is fed to the flow cell 10 via the liquid flow path 52 and the supply flow path 53. Note that the liquid feeding unit 30 may be a diaphragm pump or a reference liquid may be fed using an air pressure generated by an electropneumatic converter connected to a pressure source such as a compressor. The sheath liquid feeding unit 40 includes, for example, a syringe 41, an actuator 42 inserted into the syringe 41, and a drive device 43 such as a motor for moving the actuator 42.

When the drive device 43 pushes the actuator 42, the sheath liquid flows through the sheath liquid flow path 54 to the flow cell 10. Note that the sheath liquid feeding unit 40 may be a diaphragm pump or the sheath liquid may be fed using an air pressure generated by an electropneumatic converter connected to a pressure source such as a compressor.

The flow cell 10 is made of a transparent material such as quartz. In the flow cell 10, the flow of the reference liquid and the flow of the sheath liquid form a laminar flow, and the reference liquid flows so as to be surrounded by the flow of the sheath liquid. The sheath liquid feeding unit 40 also may feed the sheath liquid to the liquid feeding unit 30 and balance the pressure of the sheath liquid and the pressure of the reference liquid within the flow cell 10.

As shown in FIG. 2, the flow velocity measuring device 200 includes an optical system capable of measuring the flow velocity of the reference particle based on the optical characteristics of the reference particles flowing inside the flow cell 10. Note that the flow cell 10 is shown in cross section in FIG. 2. An optical system capable of measuring the flow velocity of reference particles flowing inside the flow cell 10 includes a light source 121 that irradiates light on the flow cell 10. A laser, a light emitting diode, or the like can be used as the light source 121. The light irradiated from the light source 121 is condensed by, for example, the lens 131, passes through the dichroic mirrors 141 and 142, and is focused on the flow cell 10. Scattered light is generated by particles when the reference particles flowing inside the flow cell 10 have optical characteristics to generate Mie scattered light as reactive light when irradiated with light. The scattered light having the same wavelength as the light emitted from the light source 121 is condensed by the lens 135, for example, and is reflected by the dichroic mirror 143.

Figure 7:
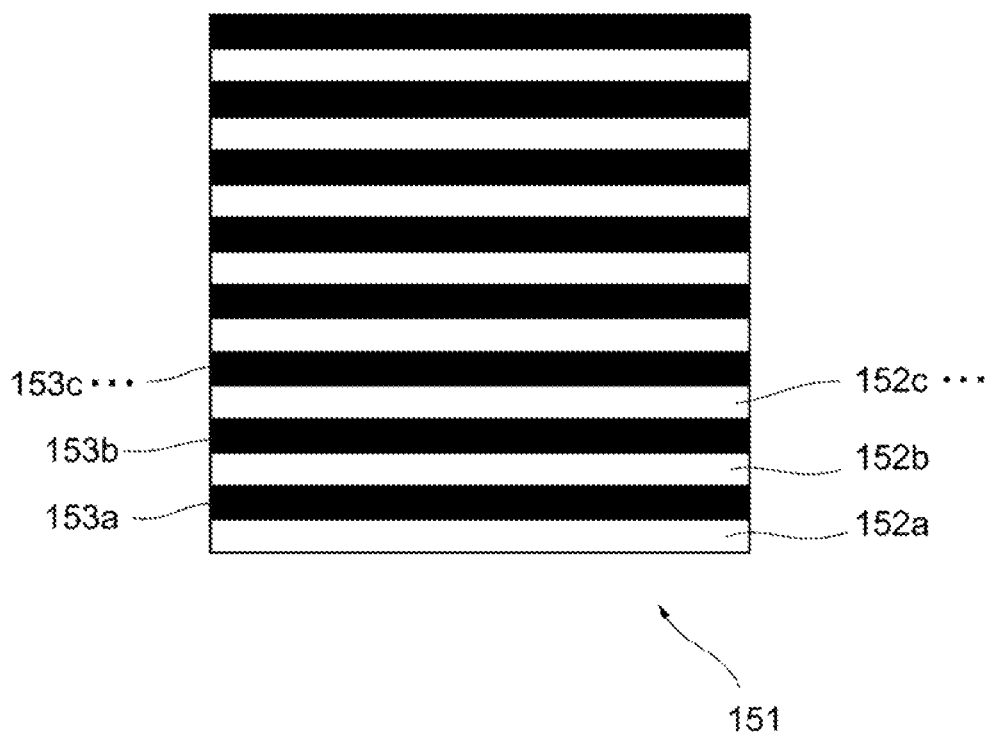
FIG. 7 is a schematic diagram showing an optical grating according to the embodiment.

An optical grating 151 is disposed in the optical path of the scattered light reflected by the dichroic mirror 143. As shown in FIG. 7, the optical grating 151 includes a plurality of transparent portions 152a, 152b, 152c, and the like, and a plurality of opaque portions 153a, 1523, 153c alternately arranged. Each of the plurality of transparent portions 152a and the like and the plurality of opaque portions 153a and the like is rectangular, for example. The pitch of the optical grating 151 is constant, and the width of each of the plurality of transparent portions 152a and the like, and the plurality of opaque portions 153a and the like is, for example, approximately the size of the reference particle flowing inside the flow cell 10 shown in FIG. 2.

When the reference particle traverses the light emitted by the light source 121 inside the flow cell 10, the scattered light generated by the reference particle is alternately crosses the plurality of transparent portions 152a and the like and the plurality of opaque portions 153a and the like of the optical grating 151 shown in FIG. 7. Therefore, the intensity of the scattered light is modulated by the optical grating 151. The modulated light of the scattered light generated by the optical grating 151 is condensed by the lens 136 shown in FIG. 2, and detected by the reactive light detection unit 161. A device including a photoelectric multiplier tube and a photoelectric conversion element such as a photodiode can be used as the reactive light detection unit 161.

The period in which the reactive light detection unit 161 detects the modulated light is proportional to the flow velocity of the reference particle flowing inside the flow cell 10. The reactive light detection unit 161 is connected to a flow velocity information calculation unit 301 shown in FIG. 1. The flow velocity information calculation unit 301 is included in the computer 300. The flow velocity information calculation unit 301 is realized in the computer 300 by the processor executing the program stored in the memory. Note that the flow velocity information calculation unit 301 may be realized by hardware such as a PLC (Programmable Logic Controller), for example. The flow velocity information calculation unit 301 specifies the cycle f by, for example, fast Fourier transform (FFT), and calculates the value of the flow velocity v of the reference particle flowing inside the flow cell 10 as information related to the flow velocity based on the following equation (1).

$$v=fp \qquad (1)$$

In equation (1), p represents the pitch of the optical grating 151. The value of the flow velocity may be an average value. The average value may be calculated by moving average. The flow velocity information calculation unit 301 also may calculate the value of the variation in the flow velocity such as the variation coefficient (CV) as the information related to the flow velocity. Alternatively, the flow velocity information calculation unit 301 may calculate both the value of the flow velocity v of the particle and the value of the variation in the flow velocity as information related to the flow velocity.

Note that the configuration of the flow velocity measuring device is not limited to the above. For example, when a known beam diameter inside the flow cell 10 of the light irradiated on the flow cell 10 is designated $D_B$, the known diameter of the reference particle is designated $D_S$, the pulse width of the scattered light generated when the reference particle traverses the beam diameter is designated $P_W$, then the flow velocity v of the particles flowing inside the flow cell 10 may be calculated based on the following expression (2).

$$v=(D_B+D_S)/P_W \qquad (2)$$

In this case, the optical grating 151 is unnecessary, and the flow velocity information calculation unit 301 may calculate the flow velocity v based on the pulse width of the reactive light detected by the reactive light detection unit 161.

Alternatively, the flow rate measuring device may comprise at least two particle detectors. In this case, the flow velocity information calculation unit 301 also may calculate the particle flow velocity v based on the known distance between the two particle detectors and the time lapse from the detection of the reference particle by the upstream particle detection unit and the detection of the reference particle by the downstream particle detection unit. Alternatively, the flow velocity measuring device may include a flowmeter provided in a flow path connected to the outlet side of the flow cell 10. In this case, the flow velocity information calculation unit 301 may calculate the flow velocity v of the particles based on the flow velocity measured by the flowmeter, the difference between the aperture of the flow cell 10 and the aperture of the flow channel, and the like.

As shown in FIG. 1, the flow cytometer according to the embodiment also includes a control unit 302 that controls the sheath liquid feeding unit 40, the liquid feeding unit 30, and the sample liquid feeding unit 20. The control unit 302 is included in the computer 300. The control unit 302 is realized, for example, in the computer 300 by the processor executing a program stored in the memory. However, the control unit 302 also may be realized by hardware such as a PLC, for example.

Figure 8:
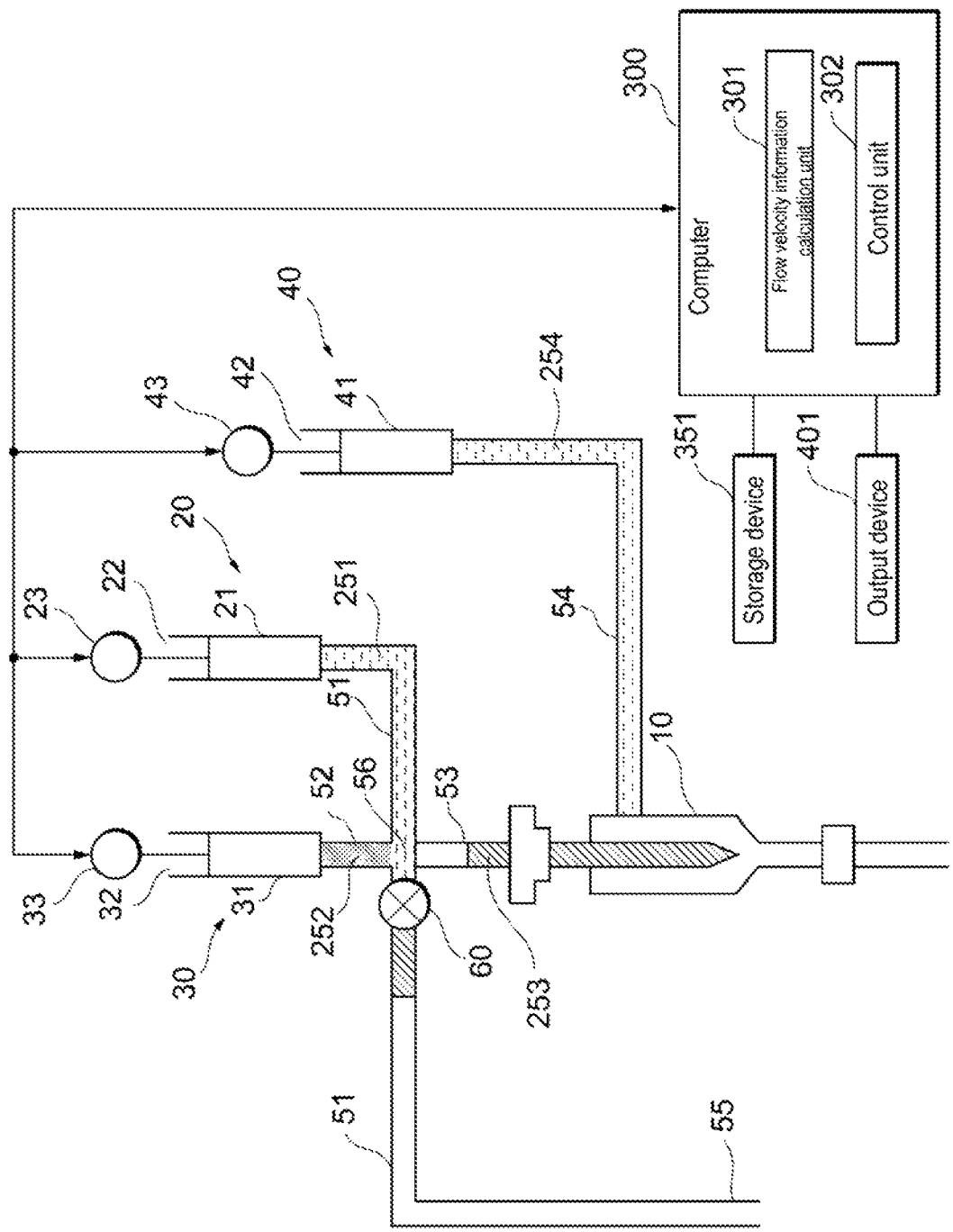
FIG. 8 is a schematic diagram showing flow paths and the like of the flow cytometer according to the embodiment.

The control unit 302 receives information related to the flow velocity from the flow velocity information calculation unit 301. When the information related to the flow velocity of the reference particles flowing through the flow cell 10 satisfies a criterion, the control unit 302 causes the sample liquid feeding unit 20 to feed the sample liquid to the flow cell 10 as shown in FIG. 8. When the drive device 23 presses the actuator 22, the sample liquid is fed to the flow cell 10 via the sample liquid flow path 51 and the supply flow path 53. When the information related to the flow velocity of the reference particles flowing through the flow cell 10 does not satisfy the criterion, the control unit 302 does not cause the sample feeding unit 20 to feed the sample liquid to the flow cell 10.

When the information related to the flow velocity is the value of the flow velocity, the fact that the information related to the flow velocity of the reference particle flowing through the flow cell 10 satisfies the criterion indicates, for example, that the value of the flow velocity of the reference particle is within a predetermined range. The predetermined range is preset, for example, on the basis of the flow velocity at which the sample particles flowing inside the flow cell 10 can be stably analyzed. When the information related to the flow velocity is the value of the variation in the flow velocity, the fact that the information related to the flow velocity of the reference particle flowing through the flow cell 10 satisfies the criterion indicates, for example, that the value of the variation in the flow velocity is a predetermined value or less. The predetermined value is preset based on, for example, the upper limit of the allowable range of fluctuation in the flow velocity at which the sample particles flowing through the flow cell 10 can be stably analyzed. When the fluctuation of the flow velocity is a variation coefficient, for example, when the variation coefficient is 0.2 or less, the control unit 302 causes the sample liquid feeding unit 20 to feed the sample liquid to the flow cell 10. However, the predetermined value is not limited to this.

Information indicating a standard relating to the flow velocity such as a predetermined range of the flow velocity value, and a predetermined upper limit value of the flow velocity variation is stored in the memory provided in the computer 300 or in the storage device 351 connected to the computer 300. This information also may be changed, for example, by input from the user.

Figure 9:
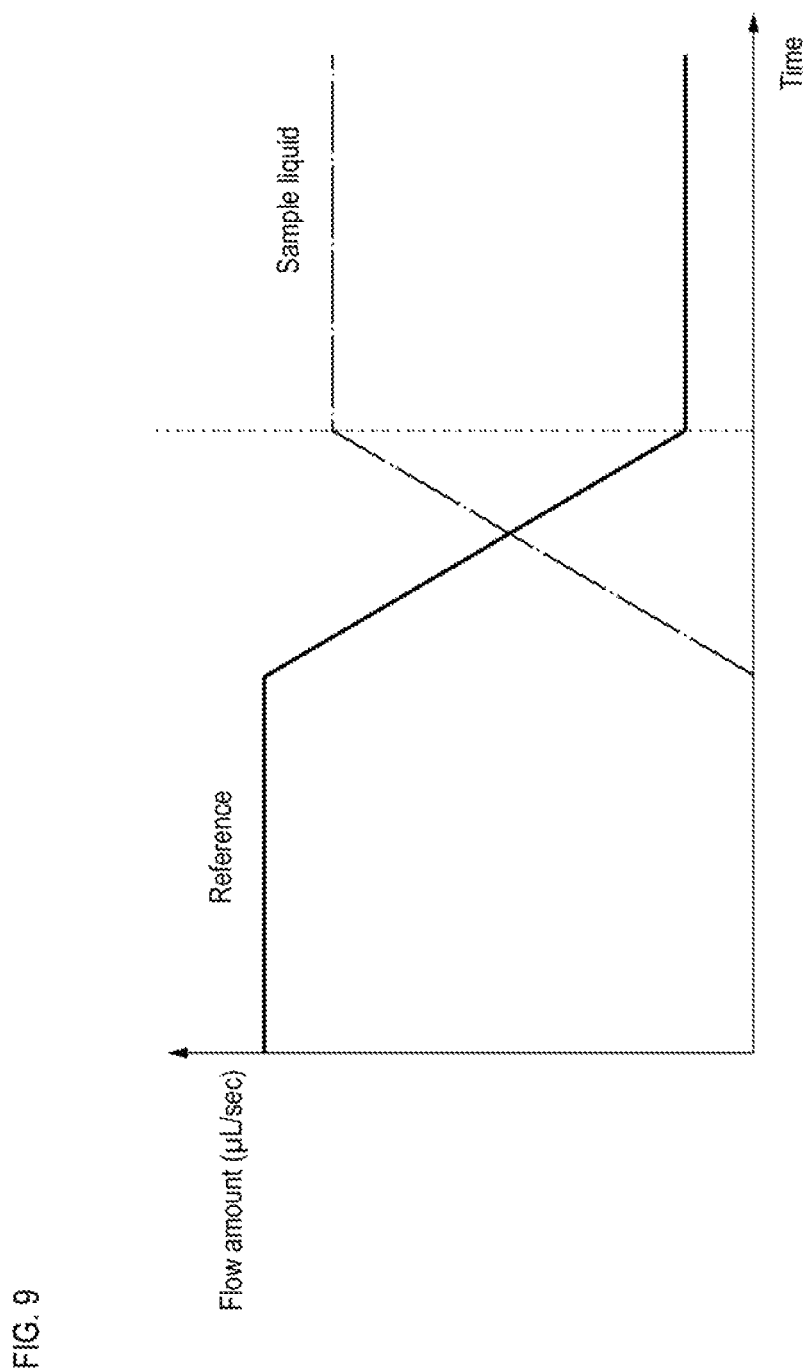
FIG. 9 is a schematic graph showing temporal changes in flow velocities of a reference solution and a sample solution in a flow cytometer according to an embodiment.

First, the liquid feeding unit 30 feeds the reference liquid to the flow cell 10, which is in a high pressure state due to the supply of the sheath liquid, at a first flow velocity of a size that prevents particles from back-flowing. This process is sometimes called pre-drive. Thereafter, the liquid feeding unit 30 feeds the reference liquid to the flow cell 10 at a second flow velocity, which is lower than the first flow velocity. Then, after the information on the flow velocity of the reference fluid meets the criterion, the sample liquid feeding unit 20 starts feeding the sample liquid to the flow cell 10, and as shown in FIG. 9, the liquid feeding unit 30 and the sample liquid feeding unit 20 decreases the flow velocity of the reference liquid and increases the flow velocity of the sample liquid so that the sum of the flow velocity of the reference liquid and the flow velocity of the sample liquid becomes the same as the second flow velocity. After the flow velocity of the sample liquid reaches the predetermined flow velocity, the liquid feeding unit 30 and the sample liquid feeding unit 20 respectively feed the reference liquid and the sample liquid at a constant flow rate. In this way it is possible to maintain the flow velocity of the sample liquid flowing through the flow cell 10 in a state satisfying the above criterion.

When the sheath liquid feeding unit 40 starts feeding the high-pressure sheath liquid, pressure variation may occur in the air layer between the sample liquid 253 and the internal liquid 251 shown in FIG. 5. However, the pressure fluctuation of the air layer is reduced while the liquid feeding unit 30 is feeding the reference liquid to the flow cell 10 at the second flow velocity.

When the optical characteristics of the reference particles are more suitable for flow velocity detection than the sample particles, and when the number of sample particles is relatively small and it is difficult to detect the flow velocity by the sample particles, it is possible to accurately monitor the flow velocity of the particles flowing inside the flow cell 10 shown in FIG. 1 by feeding a constant flow amount of the reference liquid to the flow cell 10 even after the flow velocity of the sample liquid becomes constant. The sheath liquid feeding unit 40 also may feed the sheath liquid to the sample liquid feeding unit 20, and balance the pressure of the sheath liquid and the pressure of the sample liquid inside the flow cell 10.

The flow cytometer according to the embodiment also includes an output device 401 for outputting the fact that the information on the flow velocity rate does not satisfy the criterion. The output device 401 outputs information for querying the operator whether to stop feeding the sample liquid to the flow cell 10 when the information relating the flow velocity does not satisfy the criterion. The output device 401 is, for example, a display. Note that a printer, a speaker, and the like can also be used as the output device 401. The output device 401 is connected to the computer 300. However, the output device 401 also may be located at a remote place.

As shown in FIG. 2, the detector 201 includes an optical system capable of capturing an image of sample particles flowing inside the flow cell 10. The optical system capable of capturing images of the sample particles flowing inside the flow cell 10 also includes light sources 122, 123, and 124 in addition to the light source 121 described above. The light source 121 irradiates, for example, light of a wavelength $\lambda_{E1}$ that excites GFP. When CTC is labeled with GFP, the CTC flowing inside the flow cell 10 has a green fluorescence of a wavelength $\lambda_{F1}$.

The light source 122 irradiates light of a wavelength $\lambda_{E2}$ that is different from a wavelength $\lambda_{E1}$. The light irradiated by the light source 122 is condensed by, for example, the lens 132, reflected by the dichroic mirror 141 in the direction of the flow cell 10, transmitted through the dichroic mirror 142, and reaches the flow cell 10. When the sample particles are labeled with the fluorescent dye excited by the light of the wavelength $\lambda_{E2}$ irradiated by the light source 122, the sample particles within the flow cell 10 give off fluorescent light of a wavelength $\lambda_{F2}$. Wavelength $\lambda_{F2}$ is, for example, the wavelength of red color.

The light source 123 irradiates light of a wavelength $\lambda_{E3\sim E2}$ the wavelength $\lambda_{E1\sim E2}$. The light irradiated by the light source 123 is condensed by, for example, the lens 133, reflected by the dichroic mirror 142 in the direction of the flow cell 10, and reaches the flow cell 10. When the sample particles are labeled with the fluorescent dye excited by the light of the wavelength $\lambda_{E3}$ irradiated by the light source 123, the sample particles within the flow cell 10 give off fluorescent light of a wavelength $\lambda_{F3}$. Wavelength $\lambda_{F3}$ is, for example, the wavelength of blue color.

The light source 123 irradiates light of a wavelength $\lambda_{E4}$ that is different from the wavelength $\lambda_{E1\sim E3}$. The light of wavelength $\lambda_{E4}$ is, for example, visible light. The light irradiated by the light source 124 is condensed by the lens 134, for example, and reaches the flow cell 10. The light of wavelength $\lambda_{E4}$ passes through the sample particles inside the flow cell 10.

The fluorescence of wavelength $\lambda_{F1\sim F3}$ produced by the sample particles in the flow cell 10, and the transmission light of wavelength $\lambda_{E4}$ pass through the dichroic mirror 143 via the lens 135, and reach the optical unit 144. In the optical unit 144, for example, four dichroic mirrors are combined. The four dichroic mirrors reflect the fluorescent light of wavelengths $\lambda_{F1\sim F3}\lambda$ and the transmission light of wavelength $\lambda_{E4}$ are reflected at slightly different angles from each other toward the imaging device 162. The fluorescent light of wavelength $\lambda_{F1\sim F3}$ reflected by the optical unit 144 and the transmission light of wavelength $\lambda_{E4}$ is condensed by the lens 137, and reaches a different position on the light receiving surface of the imaging device 162.

The imaging device 162 is a device including a photoelectric conversion element, for example, a TDI imaging device, and includes a CCD array. The imaging device 162 receives information related to the value of the flow velocity of the particles flowing inside the flow cell 10 from the flow velocity information calculation unit 301 shown in FIG. 1. The imaging device 162 shown in FIG. 2, in synchronization with the received value of flow velocity, generates three fluorescence images corresponding to the fluorescence of wavelengths $\lambda_{F1\sim F3}$, and a bright field image corresponding to the transmission light of wavelength $\lambda_{E4}$. When an image of sample particles emitting green fluorescence of wavelength $\lambda_{F1}$ is generated, it can be determined that the sample particle is CTC. When chromosome 17 of CTC and the Her2 gene are fluorescently stained, a cell containing a luminescent spot based on chromosome 7 and a luminescent spot based on Her 2 gene may be extracted based on 17 chromosome, and an extracted image of the cell may be analyzed to determine that the cell with amplified Her2 gene is CTC.

Figure 10:
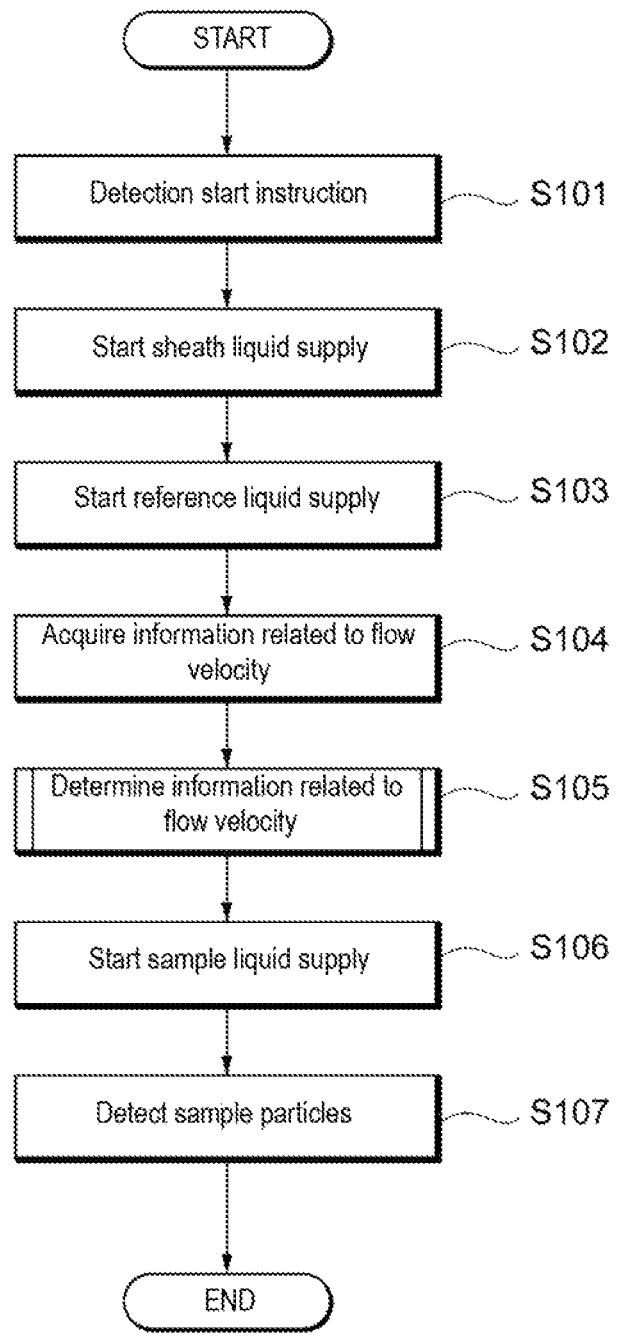
FIG. 10 is a flowchart showing a particle detection method according to an embodiment.

Next, the particle detection method according to the embodiment will be described with reference to FIGS. 10 and 11. As shown in FIG. 10, the particle detection method according to the embodiment includes a step S101 instructing a flow cytometer to start detection, a step S102 to start supply of the sheath liquid to the flow cell 10, a step S103 of starting to feed a reference liquid to the flow cell 10, a step S104 of acquiring information related to the flow velocity of the reference fluid flowing inside the flow cell 10, a step S105 of determining whether information related to the flow velocity satisfies a criterion, a step S106 of starting to feed the sample liquid to the sample cell 10, and a step S107 of detecting the sample particles flowing inside the flow cell 10.

When the detection start is instructed in step S101, the sample liquid feeding unit 20, under the control of the control unit 302, suctions the sample liquid into the sample liquid flow path 51 so as to produce an air layer between the sample liquid and the internal liquid. The sample liquid feeding unit 20 suctions the sample liquid from the connection point 56 to the sample liquid feeding unit 20 side and stops the suction. Thereafter, the valve 60 is closed under the control of the control unit 302. In step S102, the sheath fluid feeding unit 40 starts feeding the sheath fluid to the flow cell 10, under the control of the control unit 302. In step S103, the liquid feeding unit 30 starts feeding the reference liquid to the flow cell 10. Note that steps S102 and S103 may be performed at the same time.

In step S104, the light source 121 shown in FIG. 2 irradiates light on the reference particles flowing inside the flow cell 10, and the reactive light detection unit 161 detects the modulated light of the scattered light generated by the reference particle via the optical grating 151. The flow velocity information calculation unit 301 shown in FIG. 1 calculates information on the flow velocity based on the period of the modulated light. In step S105, the control unit 302 reads the information indicating the criterion related to the flow velocity from the memory, the storage device 351 or the like, and determines whether the information related to the flow velocity satisfies the criterion. When it is determined in step S201 shown in FIG. 11 that the criterion is satisfied, in step S106 of FIG. 10, the sample liquid feeding unit 20, under the control of the control unit 302, starts feeding the sample liquid to the flow cell 10, and in step S107, the imaging device 162 shown in FIG. 2 starts capturing images of the sample particles. When a predetermined amount of sample liquid is analyzed, the analysis is completed.

Figure 11:
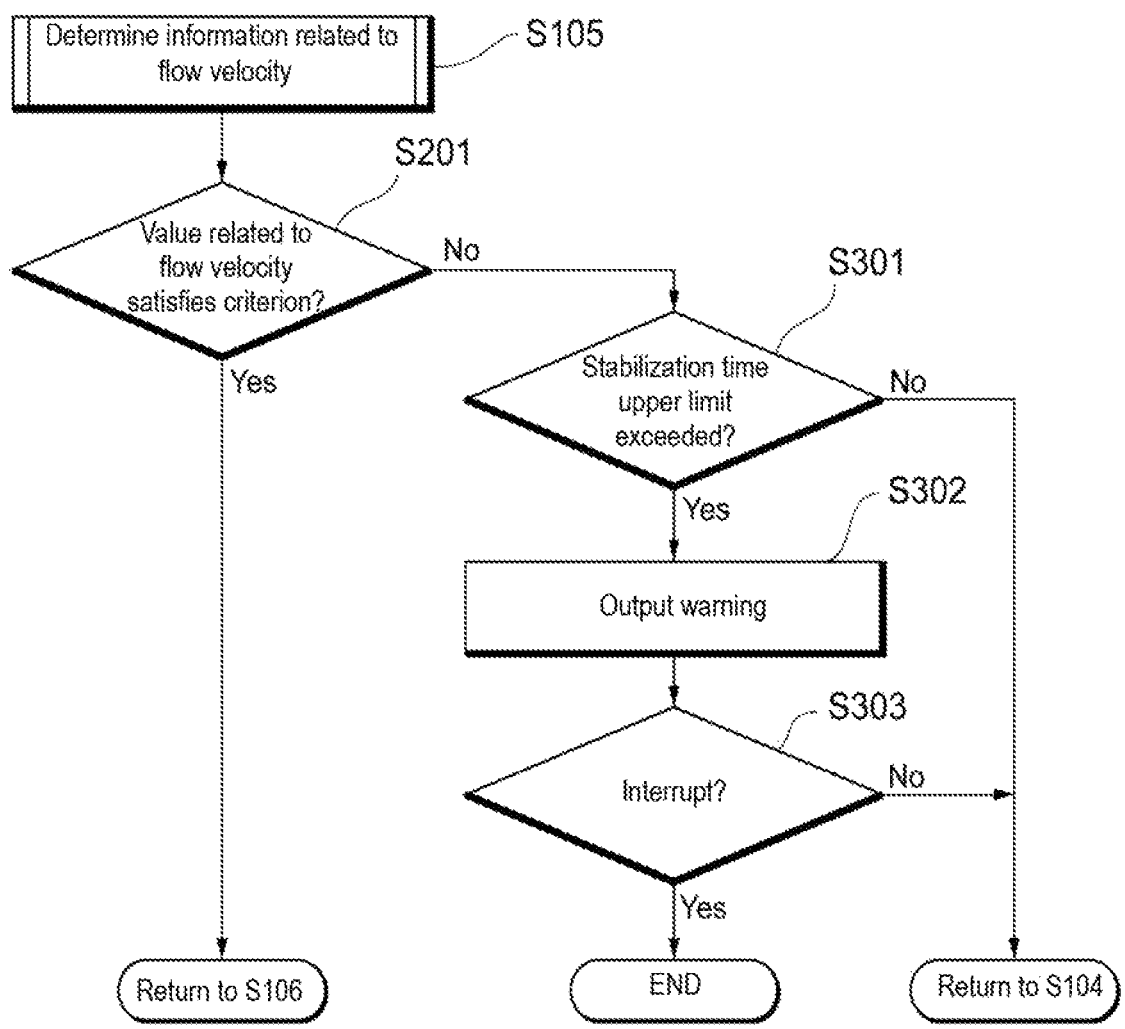
FIG. 11 is a continuation of the flowchart showing a particle detection method according to an embodiment.

When it is determined in step S201 shown in FIG. 11 that the criterion is not satisfied, then, in step S301 the control unit 302 determines whether the time from the start of liquid feed of the reference liquid exceeds the upper limit. If it is determined that the upper limit is not exceeded, the process returns to step S104 of FIG. 10 and measurement of the flow velocity of the reference particles continues. If it is determined in step S301 of FIG. 11 that the upper limit is exceeded, then, in step S302 the output device 401 outputs a warning indicating that the information on the flow velocity does not satisfy the criterion, and outputs information for querying the operator whether to stop feeding the sample liquid to the flow cell 10.

In step S303, if the operator selects not to stop feeding the sample liquid to the flow cell 10, the process returns to step S104 in FIG. 10 and measurement of the flow velocity of the reference particles continues. When the operator selects to cancel in step S303 of FIG. 11, the liquid feeding unit 30, under the control of the control unit 302, stops feeding the reference liquid to the flow cell 10. In this case, the sample liquid feeding unit 20 also may send back unused sample liquid inside the sample liquid flow path 51 and reuse the returned sample liquid.

According to the flow cytometer of the embodiment described above, it is possible to suppress the waste of the sample liquid since the sample liquid is not fed to the flow cell 10 until the information on the flow velocity of the reference particles flowing inside the flow cell 10 satisfies the criterion. After the information on the flow velocity of the reference particles flowing inside the flow cell 10 satisfies the criterion, the sample liquid is fed to the flow cell 10, and it is possible to start the analysis of the sample particles contained in the sample liquid.

For example, in the flow cytometer according to the embodiment, the reference liquid is allowed to flow through the flow cell 10 at the first flow rate of 0.0774 µL/second for 10 seconds, and thereafter, the reference liquid is flowed through the flow cells 10 at a second flow rate of 0.006 µL/second for 90 seconds. In this case, 1.3667 µL of the reference fluid flows through the flow cell 10 until the flow rate is stabilized. In a conventional flow cytometer, the same amount of sample liquid was wasted without being used for analysis, but in the flow cytometer according to the embodiment, the same amount of sample particles in the sample liquid can be used for analysis. Therefore, it is possible to detect trace amounts of samples such as CTC without wasting the sample.

The present invention has been described with reference to the embodiments as described above, but it should not be understood that the description and drawings constituting a part of this disclosure limit the present invention. From this disclosure, various alternative embodiments, examples and operational techniques will be apparent to those skilled in the art. For example, although an example in which the detected imaging target is CTC is described in the above embodiment, the detection target of the present invention is not limited to CTC. The sample particles may be biological samples such as cells and microorganisms other than CTC. An example also was described in which scattered light is used as reactive light generated by light irradiated particles in measuring the flow velocity of particles. However, when particles have optical characteristics of emitting fluorescence, fluorescence may be used as reactive light. An example in which the sample particles are optically detected also has been described in the above embodiment. In contrast, sample particles also may be detected by providing electrodes facing the flow cell and measuring a change in the electrical resistance between the electrodes as the sample particles pass between the electrodes. Thus, it should be understood that the present invention encompasses various embodiments and the like not described herein.

What is claimed is:

1. A flow cytometer comprising:
   a flow cell;
   a first liquid feeding unit comprising a pump or a pneumatic converter and configured to feed a first liquid to the flow cell;
   a flow velocity measuring device comprising a light sensor and configured to optically measure a flow velocity of the first liquid flowing through the flow cell;
   a second feeding unit comprising a pump or a pneumatic converter and configured to feed a second liquid containing a sample particle to the flow cell, wherein the second liquid feeding unit feeds the second liquid to the flow cell when the flow velocity satisfies a criterion; and
   a detector for detecting the sample particle flowing through the flow cell.

2. The flow cytometer according to claim 1, wherein the first liquid feeding unit and the second liquid feeding unit feed the first liquid and the second liquid respectively to the flow cell via a common flow path.

3. The flow cytometer according to claim 1, wherein the first liquid feeding unit is configured to feed, as the first liquid, a reference liquid containing a reference particle, different from the sample particle to the flow cell.

4. The flow cytometer according to claim 3, wherein the first liquid feeding unit feeds the reference liquid to the flow cell even after the second liquid feeding unit starts to feed the second liquid to the flow cell.

5. The flow cytometer according to claim 4, wherein
the second liquid feeding unit increases an amount of the second liquid while the first liquid feeding unit decreases an amount of the first liquid.

6. The flow cytometer according to claim 1, wherein
the first liquid feeding unit feeds the first liquid to the flow cell until the flow velocity satisfies the criterion.

7. The flow cytometer according to claim 1, wherein
the criterion to the flow velocity is at least one of a value of the flow velocity or a value of a variation of the flow velocity.

8. The flow cytometer according to claim 7, wherein,
when a value of the flow velocity is within a predetermined range, the second liquid feeding unit feeds the second liquid to the flow cell.

9. The flow cytometer according to claim 7, wherein
when a value of a variation of the flow velocity is equal to or less than a predetermined value, the second liquid feeding unit feeds the second liquid to the flow cell.

10. The flow cytometer according to claim 7, wherein
the variation of the flow velocity is a coefficient of variation of the flow velocity.

11. The flow cytometer according to claim 1, further comprising:
a control unit configured to cause the second liquid to be fed to the flow cell by the second liquid feeding unit when the information on the flow velocity satisfies the criterion, and does not cause the second liquid to be fed to the flow cell when the flow velocity does not satisfy the criterion.

12. The flow cytometer according to claim 1, further comprising:
an output device that outputs information indicating that the flow velocity does not satisfy the criterion when the flow velocity does not satisfy the criterion.

13. The flow cytometer according to claim 12, wherein
the output device outputs information for inquiring whether to stop feeding the sample liquid to the flow cell when the flow velocity does not satisfy the criterion.

14. The flow cytometer according to claim 1, wherein
the first liquid feeding unit feeds the first liquid to the flow cell at a first flow velocity, and then feeds the first liquid to the flow cell at a second flow velocity that is lower than the first flow velocity.

15. The flow cytometer according to claim 1, further comprising:
a sample liquid flow path connected to the second liquid feeding unit, through which the second liquid flows;
a liquid flow path that connects the sample liquid flow path and the first liquid feeding unit, through which the first liquid flows; and
a supply flow path for connecting the sample liquid flow path and the flow cell, through which the first liquid and the second liquid flow;
wherein the second liquid is supplied into the sample liquid flow path from an open end of the sample liquid flow path.

16. The flow cytometer according to claim 15, wherein
the first liquid feeding unit feeds the first liquid to the flow cell after the second liquid feeding unit suctions the second liquid from a connection point of the sample liquid flow path and the liquid flow path to the second liquid feeding unit side.

17. The flow cytometer according to claim 15, wherein
the second liquid feeding unit suctions air in a state in which an internal liquid fills the sample liquid flow path, and then suctions the second liquid following the air.

18. The flow cytometer according to claim 1, wherein
the flow velocity measuring device measures the flow velocity based on optical signals from particles in the first liquid flowing through the flow cell.

19. The flow cytometer according to claim 18, wherein
the flow velocity measuring device comprises:
a light source for irradiating the flow cell with light;
an optical detector that detects reactive light generated by the particles irradiated with the light inside the flow cell; and
an optical grating arranged between the flow cell and the detector to modulate the reactive light.

20. A particle detection method comprising:
feeding a first liquid to a flow cell;
measuring a flow velocity of the first liquid flowing through the flow cell;
feeding a second liquid containing a sample particle to the flow cell after the flow velocity satisfies a criterion; and
detecting the sample particle in the second liquid flowing through the flow cell.

21. A flow cytometer comprising:
a flow cell;
a first liquid feeding unit comprising a pump or a pneumatic converter and configured to feed a first liquid to the flow cell;
a second liquid feeding unit comprising a pump or a pneumatic converter and configured to feed a second liquid containing a sample particle to the flow cell;
a sample liquid flow path connected to the second liquid feeding unit, through which the second liquid flows, wherein the second liquid is supplied into the sample liquid flow path from an open end of the sample liquid flow path;
a liquid flow path that connects the sample liquid flow path and the first liquid feeding unit, through which the first liquid flows;
a supply flow path for connecting the sample liquid flow path and the flow cell, through which the first liquid and the second liquid flow; and
a detector for detecting the sample particle flowing through the flow cell,
wherein the first liquid feeding unit feeds the first liquid to the flow cell after the second liquid feeding unit suctions the second liquid from a connection point of the sample liquid flow path and the liquid flow path to the second liquid feeding unit side.

22. A flow cytometer comprising:
a flow cell;
a first liquid feeding unit comprising a pump or a pneumatic converter and configured to feed a first liquid to the flow cell;
a second liquid feeding unit comprising a pump or a pneumatic converter and configured to feed a second liquid containing a sample particle to the flow cell;
a sample liquid flow path connected to the second liquid feeding unit, through which the second liquid flows, wherein the second liquid is supplied into the sample liquid flow path from an open end of the sample liquid flow path;
a liquid flow path that connects the sample liquid flow path and the first liquid feeding unit, through which the first liquid flows;

a supply flow path for connecting the sample liquid flow path and the flow cell, through which the first liquid and the second liquid flow; and a detector for detecting the sample particle flowing through the flow cell, wherein the second liquid feeding unit suctions air in a state in which an internal liquid fills the sample liquid flow path, and then suctions the second liquid following the air.

* * * * *